(12) United States Patent
Wang

(10) Patent No.: US 11,216,945 B2
(45) Date of Patent: *Jan. 4, 2022

(54) IMAGE PROCESSING FOR CALCULATION OF AMOUNT OF CHANGE OF BRAIN

(71) Applicant: FUJIFILM Corporation, Tokyo (JP)

(72) Inventor: Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 76 days.

This patent is subject to a terminal disclaimer.

(21) Appl. No.: 16/711,367

(22) Filed: Dec. 11, 2019

(65) Prior Publication Data

US 2020/0118267 A1 Apr. 16, 2020

Related U.S. Application Data

(63) Continuation of application No. PCT/JP2018/020310, filed on May 28, 2018.

(30) Foreign Application Priority Data

Jun. 30, 2017 (JP) .............................. JP2017-129245
Jul. 28, 2017 (JP) .............................. JP2017-146568

(51) Int. Cl.
*A61B 6/00* (2006.01)
*G06T 7/62* (2017.01)
(Continued)

(52) U.S. Cl.
CPC ............. *G06T 7/0012* (2013.01); *A61B 6/501* (2013.01); *G06T 7/337* (2017.01); *G06T 7/62* (2017.01);
(Continued)

(58) Field of Classification Search
CPC ......... G06T 7/0012; G06T 7/62; G06T 7/337; G06T 2207/20021; G06T 2207/30016;
(Continued)

(56) References Cited

U.S. PATENT DOCUMENTS 8,515,200 B2 * 8/2013 Mikheev ................... G06T 7/12
382/256
10,290,105 B2 5/2019 Ishii et al.
(Continued)

FOREIGN PATENT DOCUMENTS

JP H07239935 9/1995
JP 2011010828 1/2011
(Continued)

OTHER PUBLICATIONS

Office Action of Japan Counterpart Application, with English translation thereof, dated Jun. 30, 2020, pp. 1-6.
(Continued)

*Primary Examiner* — Siamak Harandi
(74) *Attorney, Agent, or Firm* — JCIPRNET

(57) ABSTRACT

A division unit 22 divides a brain included in a first brain image into a plurality of regions by performing registration between the first brain image including a brain of a subject and a standard brain image divided into a plurality of regions. A registration unit 23 performs registration between the first brain image and a second brain image that includes the brain of the subject and has a different imaging date and time from the first brain image. A change amount acquisition unit 24 acquires the amount of change from a corresponding region in the brain included in the first brain image, for at least one region of the plurality of regions in the brain included in the second brain image, based on the registration result.

16 Claims, 6 Drawing Sheets

(51) Int. Cl.
  *G06T 7/00*  (2017.01)
  *G06T 7/33*  (2017.01)

(52) U.S. Cl.
  CPC ............... *G06T 2207/20021* (2013.01); *G06T 2207/30016* (2013.01)

(58) Field of Classification Search
  CPC ......... G06T 2207/10072; G06T 7/0016; G06T 1/00; A61B 6/501; A61B 5/055; A61B 6/03; G01T 1/161
  See application file for complete search history.

(56) References Cited

U.S. PATENT DOCUMENTS

| | | | |
|---|---|---|---|
| 2010/0195883 A1* | 8/2010 | Patriarche | G06K 9/3233 382/131 |
| 2010/0259263 A1 | 10/2010 | Holland et al. | |
| 2013/0050207 A1* | 2/2013 | Lin | G06T 17/20 345/420 |

FOREIGN PATENT DOCUMENTS

| | | |
|---|---|---|
| JP | 2013165765 | 8/2013 |
| JP | 2014042684 | 3/2014 |
| JP | 2017023457 | 2/2017 |
| WO | 2009003198 | 12/2008 |
| WO | 2015029135 | 3/2015 |

OTHER PUBLICATIONS

"Office Action of Europe Counterpart Application", dated Mar. 4, 2021, p. 1-p. 6.
Dominic Holland et al., "Subregional neuroanatomical change as a biomarker for Alzheimer's disease", Proceedings of the National Academy of Sciences(PNAS), vol. 106, No. 49, Dec. 8, 2009, pp. 20954-20959 and 6551.
Yakang Dai et al., "aBEAT: A Toolbox for Consistent Analysis of Longitudinal Adult Brain MRI", PLOS One, vol. 8, No. 4, Apr. 3, 2013, pp. 1-13.
Ohmsha, LTD., "Practice Medical Image Analysis Handbook", ISBN978-4-274-21282-6, Nov. 1, 2012, pp. 1-21.
"International Search Report (Form PCT/ISA/210) of PCT/JP2018/020310", dated Aug. 7, 2018, with English translation thereof, pp. 1-5.
"Written Opinion of the International Searching Authority (Form PCT/ISA/237) of PCT/JP2018/020310", dated Aug. 7, 2018, with English translation thereof, pp. 1-12.
"Search Report of Europe Counterpart Application", dated Mar. 30, 2020, pp. 1-8.
Simon Warfield et al., "Nonlinear Registration and Template-Driven Segmentation", Brain Warping, Jan. 1999, pp. 67-84.

\* cited by examiner

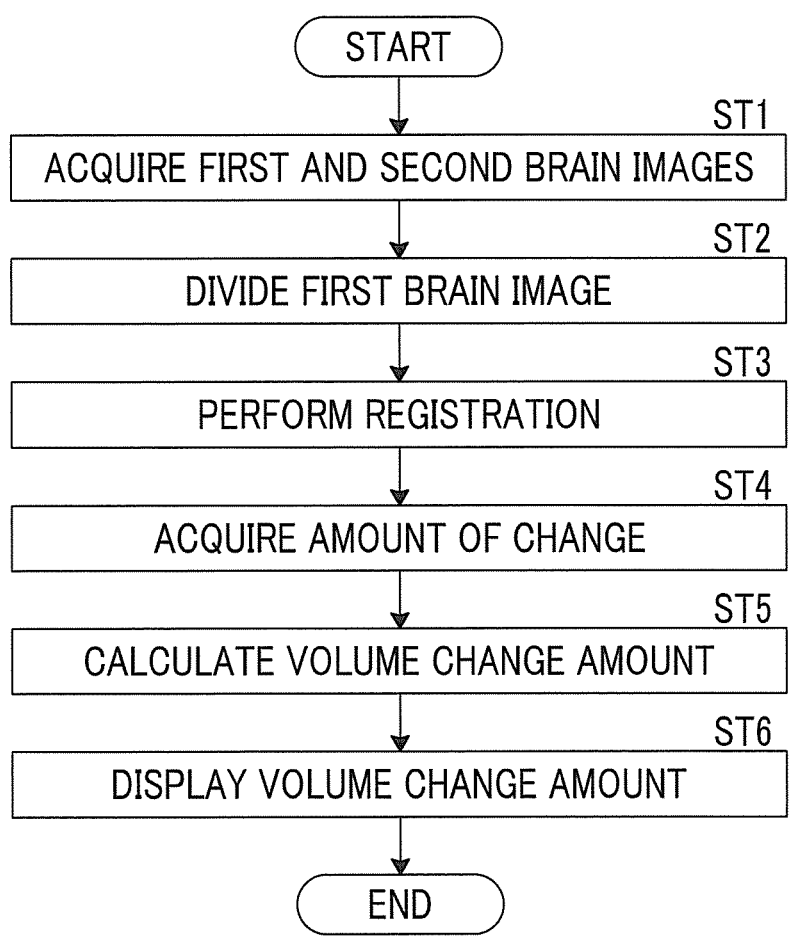

IMAGE PROCESSING FOR CALCULATION OF AMOUNT OF CHANGE OF BRAIN

CROSS REFERENCE TO RELATED APPLICATIONS

This application is a Continuation of PCT International Application No. PCT/JP2018/020310 filed on May 28, 2018, which claims priority under 35 U.S.C § 119(a) to Patent Application No. 2017-129245 filed in Japan on Jun. 30, 2017 and, Patent Application No. 2017-146568 filed in Japan on Jul. 28, 2017 all of which are hereby expressly incorporated by reference into the present application.

BACKGROUND OF THE INVENTION

1. Field of the Invention

The present invention relates to a medical image processing apparatus, a medical image processing method, and a non-transitory computer readable recording medium storing a medical image processing program for calculating the amount of change of a brain using brain images that include the brain and have different imaging dates and times for the same subject.

2. Description of the Related Art

With the arrival of an aging society, the number of patients with dementia is increasing year by year. Dementia develops in a case where a protein called amyloid β accumulates in the brain and accordingly brain atrophy progresses and cognitive ability declines. Since there is no cure for dementia, it is important in terms of maintaining the quality of life to detect brain atrophy early and start treatment early to delay the progression of dementia.

In order to meet such a demand, in recent years, information regarding the state of the brain can be acquired by nuclear medicine examinations such as single photon emission computed tomography (SPECT) and positron emission tomography (PET), CT images acquired by computerized tomography (CT) apparatuses, and MRI images acquired by magnetic resonance imaging (MRI) apparatuses. For example, decreased blood flow and metabolism in a local part of the brain can be found by checking a temporal change in the local part of the brain using SPECT and PET images.

On the other hand, brain atrophy can be found by calculating the volume of a specific part of the brain using MRI images and comparing a temporal change in the volume. For example, JP2014-042684A has proposed a method of performing registration between two brain images having different imaging dates and times and then dividing each of the two brain images into tissue regions (gray matter and white matter) and acquiring the amount of change for each tissue region.

On the other hand, for example, a method of performing registration between a brain image of a patient and a standard brain image region-divided according to the Broadmann's brain map and dividing the brain image of the patient into regions has been proposed (refer to JP2011-010828A). Here, the Broadmann's brain map shows which region in the three-dimensional region of the cerebral cortex of the standard brain controls which brain function (motion, language, perception, memory, vision, hearing, and the like). A method of acquiring the amount of change in the volume of each region after dividing the brain image of a patient into regions as described above has been proposed (Subregional neuroanatomical change as a biomarker for Alzheimer's disease, Dominic Holland et al., Proceedings of the National Academy of Sciences, Vol. 106, No. 49, pp. 20954-20959, 2009/12/8 and aBEAT: A Toolbox for Consistent Analysis of Longitudinal Adult Brain MRI, Yakang Dai et al., Alzheimer's Disease Neuroimaging Initiative, Apr. 3, 2013). In the methods described in Subregional neuroanatomical change as a biomarker for Alzheimer's disease, Dominic Holland et al., Proceedings of the National Academy of Sciences, Vol. 106, No. 49, pp. 20954-20959, 2009/12/8 and aBEAT: A Toolbox for Consistent Analysis of Longitudinal Adult Brain MRI, Yakang Dai et al., Alzheimer's Disease Neuroimaging Initiative, Apr. 3, 2013, registration between the first brain image of the patient and the standard brain image is performed to divide the first brain image into regions, and registration between the second brain image of the patient, which has a later imaging date and time than the first brain image, and the standard brain image is performed to divide the second brain image into regions. Then, the amount of change in the volume between corresponding regions in the first brain image and the second brain image is acquired.

SUMMARY OF THE INVENTION

Incidentally, the shape and size of the brain vary greatly from person to person. For example, it is known that the shape and size of an individual's brain are different from those of the standard brain by about ±15% at the maximum. For this reason, in order to perform registration between the brain image of the patient and the standard brain image, it may be necessary to greatly deform the brain image of the patient. On the other hand, the degree of brain atrophy due to dementia, that is, the amount of change in the volume of the brain is several percent per year. In the descriptions of Subregional neuroanatomical change as a biomarker for Alzheimer's disease, Dominic Holland et al., Proceedings of the National Academy of Sciences, Vol. 106, No. 49, pp. 20954-20959, 2009/12/8 and aBEAT: A Toolbox for Consistent Analysis of Longitudinal Adult Brain MRI, Yakang Dai et al., Alzheimer's Disease Neuroimaging Initiative, Apr. 3, 2013, registration between the standard brain image and each of the first and second brain images of the patient to be compared with each other is performed. In this case, as the degree of deformation for registration of each of the first and second brain images with respect to the standard brain image increases, an error due to the deformation also increases. In some cases, it is not possible to accurately obtain brain changes of only a few percent per year.

The present invention has been made in view of the above circumstances, and it is an object of the present invention to accurately acquire the amount of change between two brain images having different imaging dates and times for the same patient.

A medical image processing apparatus according to the present invention comprises: a division unit that divides a brain included in a first brain image into a plurality of regions by performing registration between the first brain image including a brain of a subject and a standard brain image divided into a plurality of regions; a registration unit that performs registration between the first brain image and a second brain image that includes the brain of the subject and has a different imaging date and time from the first brain image; and a change amount acquisition unit that acquires an amount of change from a corresponding region in the brain included in the first brain image, for at least one region of the plurality of regions in the brain included in the second brain image, based on a result of the registration between the first brain image and the second brain image.

In the medical image processing apparatus according to the present invention, the change amount acquisition unit may calculate a volume change amount for at least one region of the plurality of regions in the brain included in the second brain image.

The medical image processing apparatus according to the present invention may further comprise a display control unit that displays the volume change amount on a display unit.

In the medical image processing apparatus according to the present invention, the registration unit may acquire a movement vector between corresponding pixel positions as the amount of change between corresponding regions of the brain included in the first brain image and the brain included in the second brain image.

In the medical image processing apparatus according to the present invention, the division unit may perform second registration between the first brain image and the standard brain image after performing first registration using landmarks between the first brain image and the standard brain image.

In this case, the first registration may be registration by similarity transformation, and the second registration may be registration by nonlinear transformation.

The first registration is registration using landmarks, but the second registration is registration using any region between the standard brain image and the first brain image. The registration using any region may be, for example, registration using the entire region between the standard brain image and the first brain image or registration using only a partial region.

A "landmark" is a region having a characteristic shape in a brain image. Specifically, at least one of characteristic regions, such as a sulcus and a cerebral ventricle included in the brain, can be used as a landmark.

In the medical image processing apparatus according to the present invention, the registration unit may perform fourth registration between the first brain image and the second brain image after performing third registration using landmarks between the first brain image and the second brain image.

In this case, the third registration may be rigid registration, and the fourth registration may be registration by nonlinear transformation.

The third registration is registration using landmarks, but the fourth registration is registration using any region between the first brain image and the second brain image. The registration using any region may be, for example, registration using the entire region between the first brain image and the second brain image or registration using only a partial region.

A medical image processing method according to the present invention comprises: dividing a brain included in a first brain image into a plurality of regions by performing registration between the first brain image including a brain of a subject and a standard brain image divided into a plurality of regions; performing registration between the first brain image and a second brain image that includes the brain of the subject and has a different imaging date and time from the first brain image; and acquiring an amount of change from a corresponding region in the brain included in the first brain image, for at least one region of the plurality of regions in the brain included in the second brain image, based on a result of the registration between the first brain image and the second brain image.

In addition, a non-transitory computer readable recording medium storing a program causing a computer to execute the medical image processing method according to the present invention may be provided.

Another medical image processing apparatus according to the present invention comprises: a memory that stores commands to be executed by a computer; and a processor configured to execute the stored commands. The processor executes processing for dividing a brain included in a first brain image into a plurality of regions by performing registration between the first brain image including a brain of a subject and a standard brain image divided into a plurality of regions, performing registration between the first brain image and a second brain image that includes the brain of the subject and has a different imaging date and time from the first brain image, and acquiring an amount of change from a corresponding region in the brain included in the first brain image, for at least one region of the plurality of regions in the brain included in the second brain image, based on a result of the registration between the first brain image and the second brain image.

According to the present invention, the brain included in the first brain image is divided into a plurality of regions by performing registration between the first brain image including the brain of the subject and the standard brain image divided into the plurality of regions. Then, registration between the first brain image and the second brain image that includes the brain of the subject and has a different imaging date and time from the first brain image is performed. Based on the result of the registration between the first brain image and the second brain image, the amount of change from the corresponding region in the brain included in the first brain image for at least one region of the plurality of regions in the brain included in the second brain image is acquired. In the present invention, the second brain image is registrated with the first brain image. However, since the first and second brain images are images of the same subject, the second brain image can be accurately registrated with the first brain image even in a case where the second brain image is not deformed so much. For this reason, compared with a case where both the first brain image and the second brain image are registrated with the standard brain image, it is possible to accurately acquire a slight change amount between each region of the brain included in the first brain image and each region of the brain included in the second brain image.

BRIEF DESCRIPTION OF THE DRAWINGS

FIG. 10 is a flowchart showing the process performed in the present embodiment.

DESCRIPTION OF THE PREFERRED EMBODIMENTS

Figure 1:
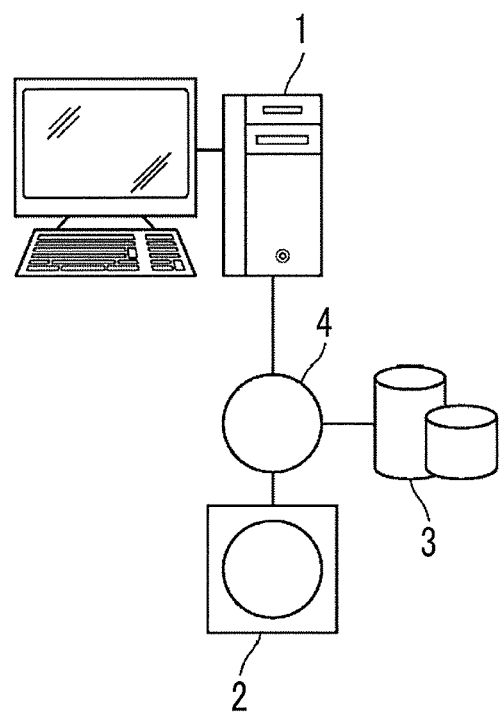
FIG. 1 is a hardware configuration diagram showing an outline of a diagnostic support system to which a medical image processing apparatus according to an embodiment of the present invention is applied.

Hereinafter, an embodiment of the present invention will be described with reference to the accompanying diagrams. FIG. 1 is a hardware configuration diagram showing the outline of a diagnostic support system to which a medical image processing apparatus according to an embodiment of the present invention is applied. As shown in FIG. 1, in the diagnostic support system, a medical image processing apparatus 1 according to the present embodiment, a three-dimensional image capturing apparatus 2, and an image storage server 3 are communicably connected to each other through a network 4.

The three-dimensional image capturing apparatus 2 is an apparatus that generates a three-dimensional image showing a part, which is an examination target part of a patient who is a subject, as a medical image by imaging the part. Specifically, the three-dimensional image capturing apparatus 2 is a CT apparatus, an MRI apparatus, a PET apparatus, or the like. The medical image generated by the three-dimensional image capturing apparatus 2 is transmitted to the image storage server 3 and is stored therein. In the present embodiment, a diagnostic target part of a patient who is a subject is a brain, the three-dimensional image capturing apparatus 2 is an MRI apparatus, and an MRI image of the head including the brain of the subject is generated as a three-dimensional brain image.

The image storage server 3 is a computer that stores and manages various kinds of data, and comprises a large-capacity external storage device and software for database management. The image storage server 3 communicates with other apparatuses through the wired or wireless network 4 to transmit and receive image data or the like. Specifically, the image storage server 3 acquires various kinds of data including image data of the medical image, which is generated by the three-dimensional image capturing apparatus 2, through the network, and stores the acquired data in a recording medium, such as a large-capacity external storage device, to manage the acquired data. The storage format of image data and the communication between devices through the network 4 are based on a protocol, such as a digital imaging and communication in medicine (DI-COM). In the present embodiment, it is assumed that a plurality of three-dimensional medical images having different imaging dates and times for the same subject are stored in the image storage server 3. In addition, it is assumed that image data of a standard brain image to be described later is also stored in the image storage server 3.

The medical image processing apparatus 1 is realized by installing a medical image processing program of the present invention on one computer. The computer may be a workstation or a personal computer that is directly operated by a doctor who performs diagnosis, or may be a server computer connected to these through a network. The medical image processing program is distributed in a state in which the medical image processing program is recorded on a recording medium, such as a digital versatile disc (DVD) or a compact disc read only memory (CD-ROM), and is installed onto the computer from the recording medium. Alternatively, the medical image processing program is stored in a storage device of a server computer connected to the network or in a network storage so as to be accessible from the outside, and is downloaded and installed onto a computer used by a doctor as necessary.

Figure 2:
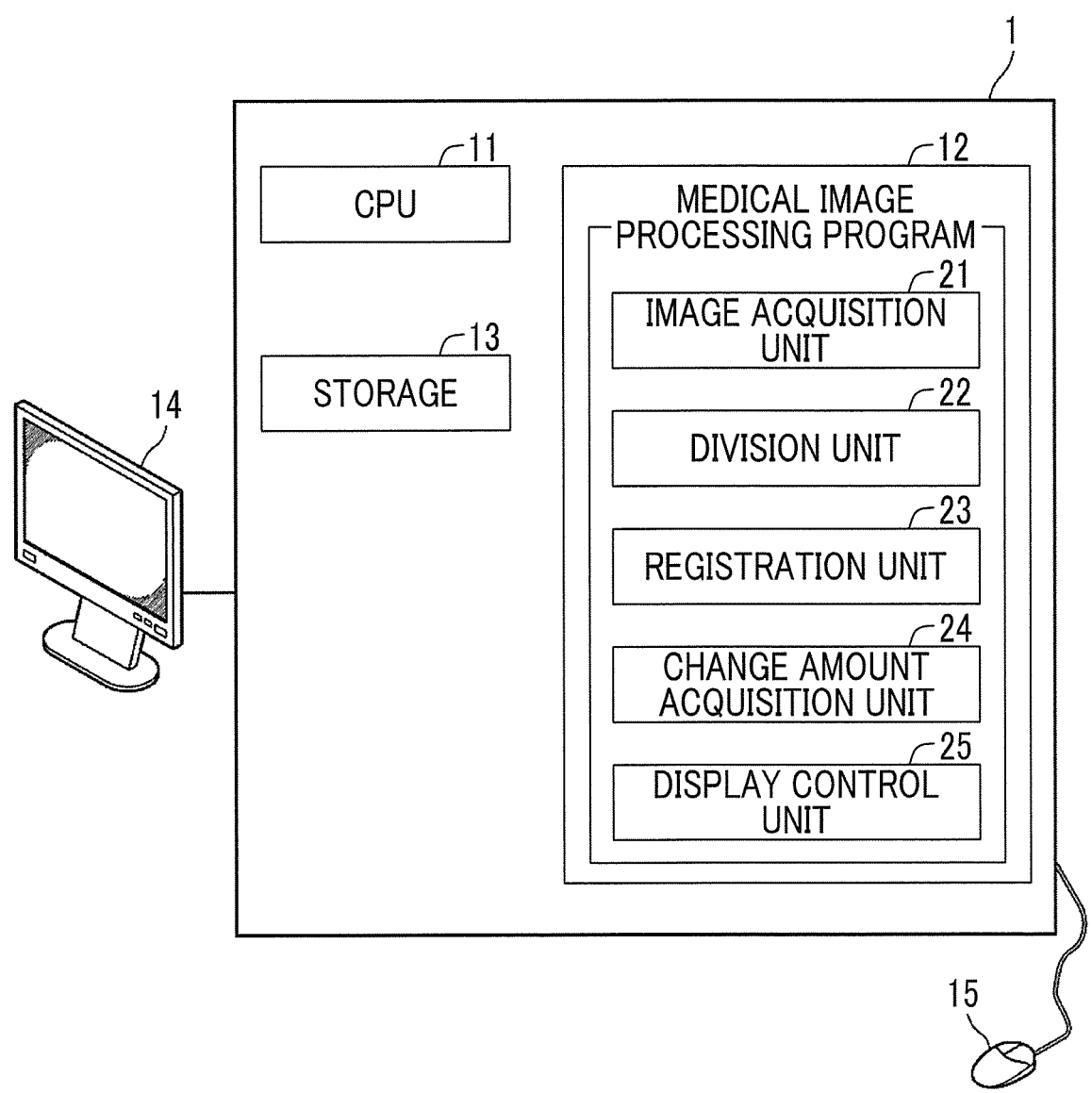
FIG. 2 is a diagram showing the schematic configuration of the medical image processing apparatus.

FIG. 2 is a diagram showing the schematic configuration of a medical image processing apparatus realized by installing a medical image processing program on a computer. As shown in FIG. 2, the medical image processing apparatus 1 comprises a central processing unit (CPU) 11, a memory 12, and a storage 13 as the configuration of a standard workstation. A display 14 and an input unit 15, such as a keyboard and a mouse, are connected to the medical image processing apparatus 1. The display 14 corresponds to a display unit.

Brain images of the subject, standard brain images to be described later, and various kinds of information including information required for processing, which are acquired from the image storage server 3 through the network 4, are stored in the storage 13.

A medical image processing program is stored in the memory 12. As processing to be executed by the CPU 11, the medical image processing program defines: image acquisition processing for acquiring first and second brain images that include the brain of the same subject and have different imaging dates and times; division processing for dividing the brain included in the first brain image into a plurality of regions by performing registration between the first brain image including the brain of the subject and a standard brain image divided into a plurality of regions; registration processing for performing registration between the first brain image and the second brain image that includes the brain of the subject and has a different imaging date and time from the first brain image; change amount acquisition processing for acquiring the amount of change from a corresponding region in the brain included in the first brain image, for at least one region of the plurality of regions in the brain included in the second brain image, based on a result of the registration between the first brain image and the second brain image; and display control processing for displaying the amount of change on the display 14.

Then, the CPU 11 executes these processes according to the program, so that the computer functions as an image acquisition unit 21, a division unit 22, a registration unit 23, a change amount acquisition unit 24, and a display control unit 25. The medical image processing apparatus 1 may comprise a plurality of processors or processing circuits that perform image acquisition processing, division processing, registration processing, change amount acquisition processing, and display control processing.

The image acquisition unit 21 acquires two brain images that include the brain of the same subject and have different imaging dates and times, that is, a first brain image B1 and a second brain image B2 from the image storage server 3. In a case where the first and second brain images B1 and B2 are already stored in the storage 13, the image acquisition unit 21 may acquire the first and second brain images B1 and B2 from the storage 13. It is assumed that the first brain image B1 has an imaging date and time earlier than that of the second brain image B2. In the present embodiment, those stored in the image storage server 3 are brain images acquired by imaging the head of the subject, and include structures other than the brain, such as a skull. The image acquisition unit 21 also acquires a standard brain image Bs from the image storage server 3.

The division unit 22 divides the brain included in the first brain image B1 into a plurality of regions by performing registration between the first brain image B1 and the standard brain image Bs divided into a plurality of regions. The standard brain image Bs is a three-dimensional brain image showing a brain having a standard shape and size and a standard density (pixel value), that is, a standard brain. The standard brain image Bs can be generated by extracting brains from a plurality of brain images, which are acquired by imaging the heads of a plurality of healthy persons with a three-dimensional image capturing apparatus, and averaging the plurality of extracted brains. The standard brain image Bs may be created by computer graphics or the like. Alternatively, a brain image of one healthy person may be used as the standard brain image Bs.

Figure 3:
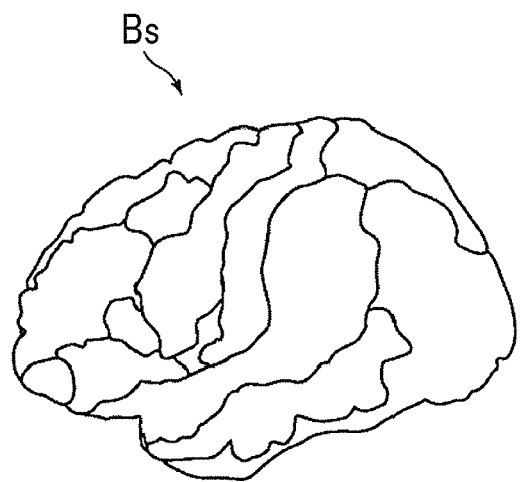
FIG. 3 is a drawing showing a standard brain image.

In the present embodiment, the standard brain image Bs is divided into a plurality of regions. As a method of division, for example, based on the Broadmann's brain map, within the three-dimensional region of the cerebral cortex, it is possible to use a method of dividing the cerebral cortex into regions responsible for functions, such as movement, language, perception, memory, vision sense, and acoustic sense. In addition, it is possible to use any known method, such as a method for division into six kinds of regions of cerebrum, diencephalon, mesencephalon, hindbrain, cerebellum, and medulla oblongata and a method of dividing the cerebrum into frontal lobe, parietal lobe, temporal lobe, and occipital lobe. Alternatively, a method of simply dividing the brain at equal intervals may be used. FIG. 3 is a diagram showing an example of a standard brain image. In FIG. 3, the standard brain image Bs is divided into a plurality of regions according to Brodmann's brain map.

Figure 4:
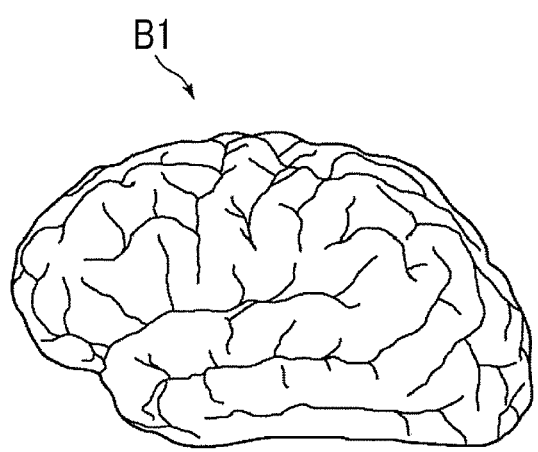
FIG. 4 is a diagram showing a first brain image.

The size and shape of the brain vary from person to person. For example, in a case where the brain is compared with the standard brain, the size and shape of the brain are different by about ±15% at the maximum. FIG. 4 is a diagram showing the first brain image B1. As shown in FIG. 4, the first brain image B1 has a different shape and size from the standard brain image Bs shown in FIG. 3. In order to divide the first brain image B1 into a plurality of regions, the division unit 22 performs first registration using landmarks between the first brain image B1 and the standard brain image Bs. Then, after performing the first registration, second registration using the entire region is performed between the first brain image B1 and the standard brain image Bs. As a landmark, specifically, at least one of characteristic regions, such as a sulcus and a cerebral ventricle included in the brain, can be used. In the present embodiment, the following description will be given on the assumption that the standard brain image Bs is registrated with the first brain image B1. However, the first brain image B1 may be registrated with the standard brain image Bs.

For registration, the division unit 22 extracts landmarks from the first brain image B1 and the standard brain image Bs. For example, landmarks may be extracted by template matching using a template indicating a landmark, or may be extracted using a discriminator that has been learned to discriminate landmarks included in an image. The division unit 22 performs the first registration between the first brain image B1 and the standard brain image Bs so that the corresponding landmarks match each other. In the present embodiment, the first registration is registration by similarity transformation. Specifically, the first registration is registration by parallel movement, rotation, and similar enlargement and reduction of the standard brain image Bs. The division unit 22 performs the first registration by performing similarity transformation of the standard brain image Bs so that the correlation between the landmark included in the standard brain image Bs and the corresponding landmark included in the first brain image B1 is maximized.

After performing the first registration using the landmarks as described above, the division unit 22 performs the second registration using the entire region between the first brain image B1 and the standard brain image Bs. In the present embodiment, the second registration is registration by nonlinear transformation. As the registration by nonlinear transformation, for example, there is registration performed by nonlinearly converting pixel positions using functions, such as B spline and thin plate spline. The division unit 22 performs the second registration by nonlinearly converting each pixel position of the standard brain image Bs after the first registration into a corresponding pixel position included in the first brain image B1.

Figure 5:
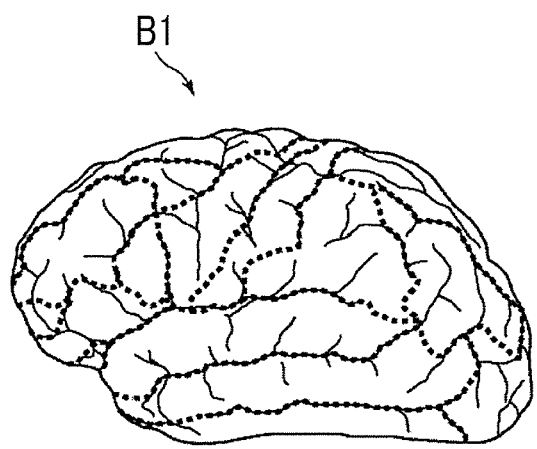
FIG. 5 is a diagram showing a first brain image divided into a plurality of regions.

By registrating the standard brain image Bs with the first brain image B1 as described above and applying the boundary between divided regions in the standard brain image Bs to the first brain image B1, the division unit 22 divides the first brain image B1 into a plurality of regions, as shown in FIG. 5.

The registration unit 23 performs registration between the first brain image B1 and the second brain image B2 that includes the brain of the subject and has a different imaging date and time from the first brain image B1. Specifically, after performing third registration using the landmarks between the first brain image B1 and the second brain image B2, fourth registration using the entire region is performed between the first brain image B1 and the second brain image B2. Although the present embodiment has been described given on the assumption that the first brain image B1 is registrated with the second brain image B2, the second brain image B2 may be registrated with the first brain image B1.

For registration, the registration unit 23 extracts landmarks from the first brain image B1 and the second brain image B2. The landmark extraction may be performed in the same manner as the first registration in the division unit 22. The registration unit 23 performs the third registration between the first brain image B1 and the second brain image B2 so that the corresponding landmarks match each other. Here, the brain included in the first brain image B1 and the brain included in the second brain image B2 have the same size since the subject is the same. Therefore, in the present embodiment, rigid registration using only parallel movement and rotation is performed as the third registration.

Figure 6:
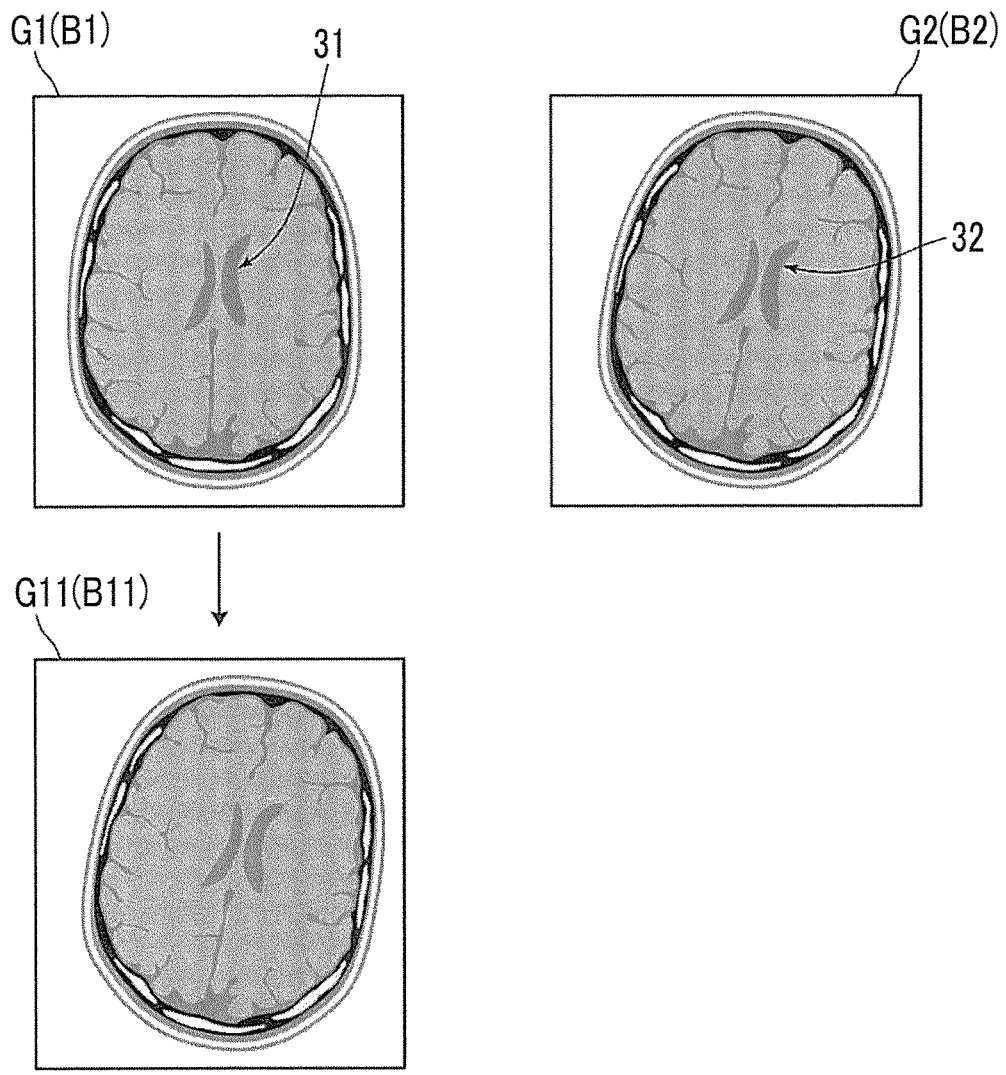
FIG. 6 is a diagram illustrating registration.

FIG. 6 is a diagram illustrating rigid registration. In FIG. 6, for the sake of description, slice images G1 and G2 of the corresponding tomographic planes in the first and second brain images B1 and B2 are shown. As shown in FIG. 6, the registration unit 23 performs the third registration, which is rigid registration, by performing parallel movement and rotation of the first brain image B1 so that the correlation between a cerebral ventricle 31, which is one of the landmarks of the slice image G1 of the first brain image B1, and a corresponding cerebral ventricle 32 included in the slice image G2 of the second brain image B2 is maximized. Therefore, a first brain image B11 (in FIG. 6, a slice image G11) subjected to the third registration is acquired.

Figure 7:
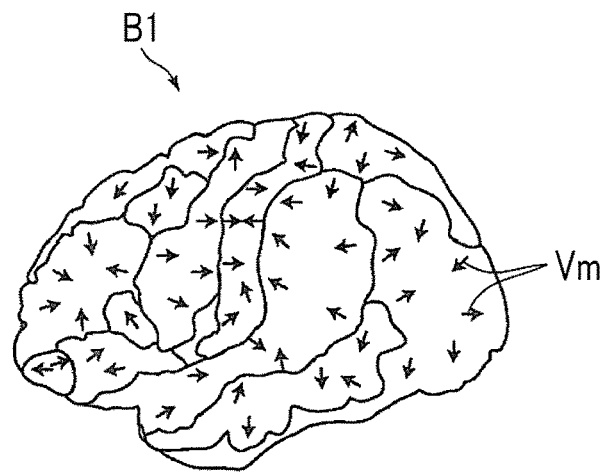
FIG. 7 is a diagram showing a movement vector.

After performing the third registration using the landmarks as described above, the registration unit 23 performs fourth registration using the entire region between the first brain image B1 and the second brain image B2. In the present embodiment, the fourth registration is registration by nonlinear transformation. The fourth registration may be performed in the same manner as the second registration in the division unit 22. Therefore, a movement vector of each pixel of the first brain image B1 to the corresponding pixel position of the second brain image B2 is acquired. FIG. 7 is a diagram showing a movement vector. As shown in FIG. 7, a movement vector Vm is acquired at each pixel position of the brain in the first brain image B1.

The change amount acquisition unit 24 acquires the amount of change from a corresponding region in the brain included in the first brain image B1, for at least one region of the plurality of regions in the brain included in the second brain image B2, based on the registration result of the registration unit 23. In the present embodiment, it is assumed that the amount of change for each of a plurality of regions is acquired. In the present embodiment, the movement vector Vm is acquired at each pixel position of the brain included in the first brain image B1 by the registration of the registration unit 23. The change amount acquisition unit 24 classifies the movement vector Vm at each pixel position of the brain included in the first brain image B1 into a plurality of regions in the first brain image B1. Therefore, for each of the plurality of regions in the brain included in the second brain image B2, the amount of change from a corresponding region in the brain included in the first brain image B1 is acquired. In this case, the amount of change is the movement vector Vm of a corresponding pixel in a corresponding region. In addition, the change amount acquisition unit 24 calculates a volume change amount for each of the plurality of regions in the brain included in the second brain image B2.

Figure 8:
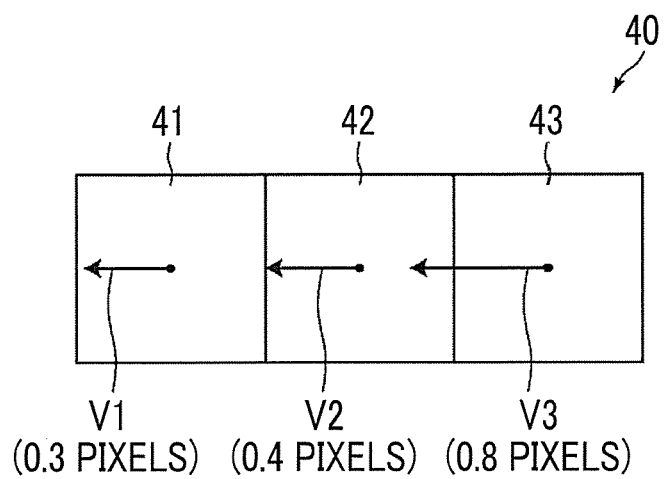
FIG. 8 is a diagram illustrating the calculation of a volume change amount.

FIG. 8 is a diagram illustrating the calculation of the volume change amount. Here, for the sake of description, it is assumed that one region 40 included in the first brain image B1 includes three pixels 41, 42, and 43 and the pixels have not moved in the vertical direction in FIG. 8. In a region A1 configured to include the three pixels 41, 42, and 43 in the first brain image B1, it is assumed that a movement vector V1 of the pixel 41 has a size of 0.3 pixel in the left direction, a movement vector V2 of the pixel 42 has a size of 0.4 pixel in the left direction, and a movement vector V3 of the pixel 43 has a size of 0.8 pixel in the left direction.

In this case, the entire region 40 is moved to the left. The interval between the pixel 41 and the pixel 42 is reduced by 0.1 pixel. The interval between the pixel 42 and the pixel 43 is reduced by 0.4 pixel. Therefore, the change amount acquisition unit 24 calculates the amount of change in the pixel value of each region 40 as −0.5 pixel. In practice, the change amount acquisition unit 24 calculates the amount of change in the pixel value in each of the directions of the three axes of x, y, and z for each region in the first brain image B1. The region atrophies in a case where the amount of change is a negative value, and expands in a case where the amount of change is a positive value.

The change amount acquisition unit 24 further calculates a volume change amount as follows. That is, for each region in the first brain image B1, the amount of change calculated for each of the directions of the three axes of x, y, and z is added. Then, by dividing the added value obtained in this manner by the total number of pixels in the corresponding region, the volume change rate of the region is calculated as the volume change amount. In this case, the volume change amount is expressed as a change rate (for example, percentage) with respect to the volume of each region. The volume change amount is also a negative value in a case where the region atrophies, and is a positive value in a case where the region expands. Here, the absolute value of the volume change amount, which is a negative value, is the atrophy rate of the brain.

For each region in the first brain image B1, an added value obtained by adding the amount of change calculated for each of the directions of the three axes of x, y, and z may be calculated as the volume change amount. In this case, the volume change amount is expressed by the magnitude of the pixel value, and the volume change amount is a negative value in a case where the region atrophies and is a positive value in a case where the region expands.

In the first and second brain images B1 and B2, the volume per pixel (that is, one voxel) is known in advance. For this reason, the amount of change calculated for each of the directions of the three axes of x, y, and z may be added, and the volume change amount may be calculated by multiplying the added value obtained in this manner by the volume per pixel. In this case, the volume change amount is expressed by the magnitude of the amount of change in the volume.

The change amount acquisition unit 24 compares the absolute value of the volume change amount, that is, the atrophy rate of the brain with a threshold value Th1 for a region having a negative value, and specifies a region having an absolute value of the volume change amount larger than the threshold value as an abnormal region and assigns a label. Here, the atrophy rate of the brain due to human aging is less than 1% per year, but is about 1% to 3% in the case of a patient with dementia. For this reason, the change amount acquisition unit 24 sets, for example, the threshold value Th1 to −1%, and specifies a region having an absolute value of the volume change amount larger than the threshold value Th1 as an abnormal region.

Figure 9:
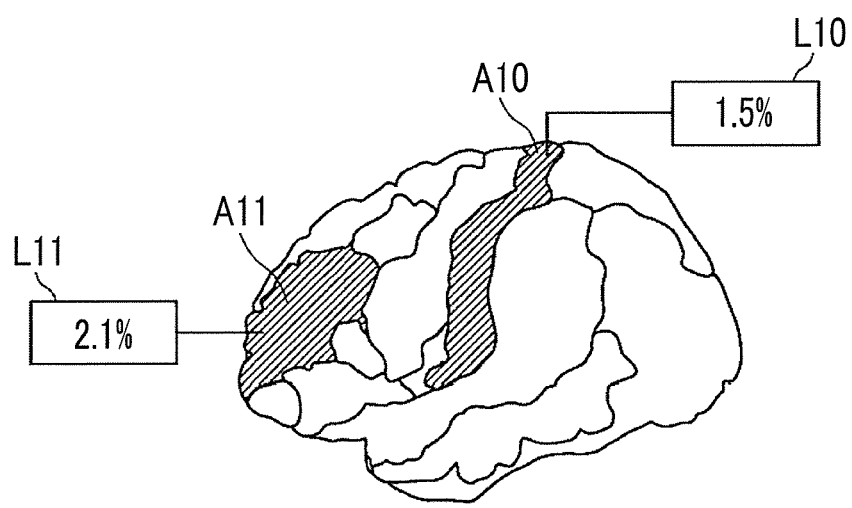
FIG. 9 is a diagram illustrating the display of a volume change amount.

The display control unit 25 displays the volume change amount on the display 14. FIG. 9 is a diagram illustrating the display of the volume change amount. As shown in FIG. 9, on the display 14, diagonal lines are given to abnormal regions A10 and A11 among the plurality of regions of the brain, and labels L10 and L11 indicating the volume change amount are given to. In FIG. 9, the labels L10 and L11 indicate the absolute value of the volume change amount, that is, the atrophy rate of the brain. Each region may be displayed in different colors according to the magnitude of the volume change amount.

Here, a region determined to have a large amount of change in the brain, that is, a large atrophy rate is displayed in an identifiable manner on the assumption that a doctor makes a diagnosis. However, the presence or absence of the occurrence of dementia may be automatically determined, and the result may be displayed. In this case, a discriminator is created by performing machine learning for a plurality of past patients using the amount of change for each region, that is, the atrophy rate and the presence or absence of the occurrence of dementia as teacher data (data with correct answers). Then, the amount of change, that is, the atrophy rate for each region of a new patient calculated in the present embodiment may be input to the discriminator to determine whether or not the new patient has dementia.

In addition, among the divided regions of the brain, a region considered to have a particularly large influence on a disease to be diagnosed may be handled differently from other regions. For example, in a case where a region determined to have a large brain atrophy rate is displayed in an identifiable manner, a region considered to have a particularly large influence on a disease to be diagnosed may be displayed in an identifiable manner from other regions. In the case of automatically determining the presence or absence of the occurrence of dementia as described above, the weight of the teacher data may be increased for a region considered to have a particularly large influence on a disease to be diagnosed at the time of making the discriminator learned. Examples of a part having a particularly large influence on a disease include a hippocampus, a cerebellum, and a temporal lobe.

Next, a process performed in the present embodiment will be described. FIG. 10 is a flowchart showing the process performed in the present embodiment. First, the image acquisition unit 21 acquires the first brain image B1 and the second brain image B2 that have different imaging dates and times for the same subject and include the brain of the subject (step ST1). Then, the division unit 22 divides the brain included in the first brain image B1 into a plurality of regions by performing registration between the first brain image B1 and the standard brain image Bs divided into a plurality of regions (step ST2). Then, the registration unit 23 performs registration between the second brain image B2 and the first brain image B1 (step ST3).

Then, the change amount acquisition unit 24 acquires the amount of change from a corresponding region in the brain included in the first brain image B1, for at least one region of the plurality of regions in the brain included in the second brain image B2, based on the registration result (step ST4). Then, the change amount acquisition unit 24 calculates a volume change amount for at least one region of the plurality of regions in the brain included in the second brain image B2 (step ST5). Then, the display control unit 25 displays the volume change amount on the display 14 (step ST6), and the process is ended.

As described above, in the present embodiment, the second brain image B2 is registrated with the first brain image B1. However, since the first and second brain images B1 and B2 are images of the same subject, the second brain image B2 can be accurately registrated with the first brain image B1 even in a case where the second brain image B2 is not deformed so much. For this reason, compared with a case where both the first brain image B1 and the second brain image B2 are registrated with the standard brain image Bs, it is possible to accurately acquire a slight change amount between each region of the brain included in the first brain image B1 and each region of the brain included in the second brain image B2. Therefore, it is possible to accurately acquire the amount of change and the volume change amount between the two brain images B1 and B2 having different imaging dates and times for the same patient.

In addition, by performing the second registration and the fourth registration that are the registration of the entire region between images after performing the first registration and the third registration using landmarks, further registration is performed after registration using a region for which registration is easy, which is called a landmark, is performed. For this reason, it is possible to efficiently perform the registration between the first brain image and the standard brain image and the registration between the first brain image and the second brain image.

In the embodiment described above, rigid registration is performed as the third registration. However, the first brain image B1 and the second brain image B2 may include brains having different sizes. In such a case, as the third registration, enlargement and reduction may be performed in addition to the rigid registration.

In the embodiment described above, the volume change amount is calculated. However, only the amount of change of each region may be calculated.

In the embodiment described above, the division unit 22 performs the second registration after performing the first registration using the landmarks. However, only the second registration, that is, registration by nonlinear transformation may be performed.

In the embodiment described above, the registration unit 23 performs the fourth registration after performing the third registration using the landmarks. However, only the fourth registration, that is, registration by nonlinear transformation may be performed.

In the embodiment described above, registration using the entire regions of the standard brain image Bs and the first brain image B1 is performed as the second registration. However, registration using the regions of parts of the standard brain image Bs and the first brain image B1 may be performed. For example, registration may be performed using only individual divided regions in the brain.

In the embodiment described above, registration using the entire regions of the first brain image B1 and the second brain image B2 is performed as the fourth registration. However, registration using the regions of parts of the first brain image B1 and the second brain image B2 may be performed. For example, registration may be performed using only individual divided regions in the brain.

In the embodiment described above, the MRI image of the subject is used as a medical image. However, brain images other than the MRI image, such as a CT image and a PET image, may be used.

Hereinafter, the effect of the present embodiment will be described.

By acquiring the volume change amount in at least one region of the plurality of regions for the brain included in the second brain image, it is possible to accurately acquire the volume change amount of each region.

By performing the second registration after performing the first registration using landmarks, further registration is performed after registration using a region for which registration is easy, which is called a landmark, is performed. For this reason, it is possible to efficiently perform registration between the first brain image and the standard brain image.

By performing the fourth registration after performing the third registration using landmarks, further registration is performed after registration using a region for which registration is easy, which is called a landmark, is performed. For this reason, it is possible to efficiently perform registration between the first brain image and the second brain image.

EXPLANATION OF REFERENCES

1: medical image processing apparatus
2: three-dimensional image capturing apparatus
3: image storage server
4: network
11: CPU
12: memory
13: storage
14: display
15: input unit
21: image acquisition unit
22: division unit
23: registration unit
24: change amount acquisition unit
25: display control unit
31, 32: cerebral ventricle
40: region
41, 42, 43: pixel
B1: first brain image
B2: second brain image
Bs: standard brain image
G1, G2, G11: slice image
L10, L11: label
Vm: movement vector

What is claimed is:

1. A medical image processing apparatus, comprising:
a processor, configured to:
divide a brain included in a first brain image into a plurality of regions by performing registration between the first brain image including a brain of a subject and a standard brain image divided into a plurality of regions;

perform registration between the first brain image and a second brain image that includes the brain of the subject and has a different imaging date and time from the first brain image; and acquire an amount of change from a corresponding region in the brain included in the first brain image, for at least one region of the plurality of regions in the brain included in the second brain image, based on a result of the registration between the first brain image and the second brain image, wherein the processor acquires a movement vector between corresponding pixel positions as the amount of change between corresponding regions of the brain included in the first brain image and the brain included in the second brain image.

2. The medical image processing apparatus according to claim 1, wherein the processor calculates a volume change amount for at least one region of the plurality of regions in the brain included in the second brain image.

3. The medical image processing apparatus according to claim 2, wherein the processor further displays the volume change amount on a display.

4. The medical image processing apparatus according to claim 1, wherein the processor performs second registration between the first brain image and the standard brain image after performing first registration using landmarks between the first brain image and the standard brain image.

5. The medical image processing apparatus according to claim 2, wherein the processor performs second registration between the first brain image and the standard brain image after performing first registration using landmarks between the first brain image and the standard brain image.

6. The medical image processing apparatus according to claim 3, wherein the processor performs second registration between the first brain image and the standard brain image after performing first registration using landmarks between the first brain image and the standard brain image.

7. The medical image processing apparatus according to claim 4, wherein the first registration is registration by similarity transformation, and the second registration is registration by nonlinear transformation.

8. The medical image processing apparatus according to claim 5, wherein the first registration is registration by similarity transformation, and the second registration is registration by nonlinear transformation.

9. The medical image processing apparatus according to claim 6, wherein the first registration is registration by similarity transformation, and the second registration is registration by nonlinear transformation.

10. The medical image processing apparatus according to claim 1, wherein the processor performs fourth registration between the first brain image and the second brain image after performing third registration using landmarks between the first brain image and the second brain image.

11. The medical image processing apparatus according to claim 2, wherein the processor performs fourth registration between the first brain image and the second brain image after performing third registration using landmarks between the first brain image and the second brain image.

12. The medical image processing apparatus according to claim 3, wherein the registration unit performs fourth registration between the first brain image and the second brain image after performing third registration using landmarks between the first brain image and the second brain image.

13. The medical image processing apparatus according to claim 10, wherein the third registration is rigid registration, and the fourth registration is registration by nonlinear transformation.

14. The medical image processing apparatus according to claim 11, wherein the third registration is rigid registration, and the fourth registration is registration by nonlinear transformation.

15. A medical image processing method, comprising:

dividing a brain included in a first brain image into a plurality of regions by performing registration between the first brain image including a brain of a subject and a standard brain image divided into a plurality of regions;

performing registration between the first brain image and a second brain image that includes the brain of the subject and has a different imaging date and time from the first brain image; and acquiring an amount of change from a corresponding region in the brain included in the first brain image, for at least one region of the plurality of regions in the brain included in the second brain image, based on a result of the registration between the first brain image and the second brain image, wherein a movement vector between corresponding pixel positions is acquired as the amount of change between corresponding regions of the brain included in the first brain image and the brain included in the second brain image.

16. A non-transitory computer readable recording medium storing a medical image processing program causing a computer to execute:

a step of dividing a brain included in a first brain image into a plurality of regions by performing registration between the first brain image including a brain of a subject and a standard brain image divided into a plurality of regions;

a step of performing registration between the first brain image and a second brain image that includes the brain of the subject and has a different imaging date and time from the first brain image; and a step of acquiring an amount of change from a corresponding region in the brain included in the first brain image, for at least one region of the plurality of regions in the brain included in the second brain image, based on a result of the registration between the first brain image and the second brain image, wherein a movement vector between corresponding pixel positions is acquired as the amount of change between corresponding regions of the brain included in the first brain image and the brain included in the second brain image.

* * * * *